US00PP13794P39

(12) United States Plant Patent
Pieters

(10) Patent No.: US PP13,794 P3
(45) Date of Patent: May 13, 2003

(54) CHRYSANTHEMUM PLANT NAMED 'GEDI ONE CAR'

(75) Inventor: Dirk Pieters, Staden (BE)

(73) Assignee: Pieters Plant Production, Bvb, Oostnieuwkerke (BE)

( * ) Notice: Subject to any disclaimer, the term of this patent is extended or adjusted under 35 U.S.C. 154(b) by 0 days.

(21) Appl. No.: 09/873,904

(22) Filed: Jun. 4, 2001

(65) Prior Publication Data

US 2002/0184678 P1 Dec. 5, 2002

(51) Int. Cl.[7] ..... A01H 5/00
(52) U.S. Cl. ..... Plt./287

(58) Field of Search ..... Plt./287, 292, 286

(56) References Cited

U.S. PATENT DOCUMENTS

PP11,300 P 3/2000 Boeder ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a large decorative type inflorescence, consistent flowering response to short days, blooming consistently after 49 days of short day length, free branching habit, and dark purple ray florets, which resist fading with age.

1 Drawing Sheet

LATIN NAME

*Dendranthema morifolium*

VARIETY

'GEDI ONE CAR'

BACKGROUND OF THE INVENTION

Figure 1:
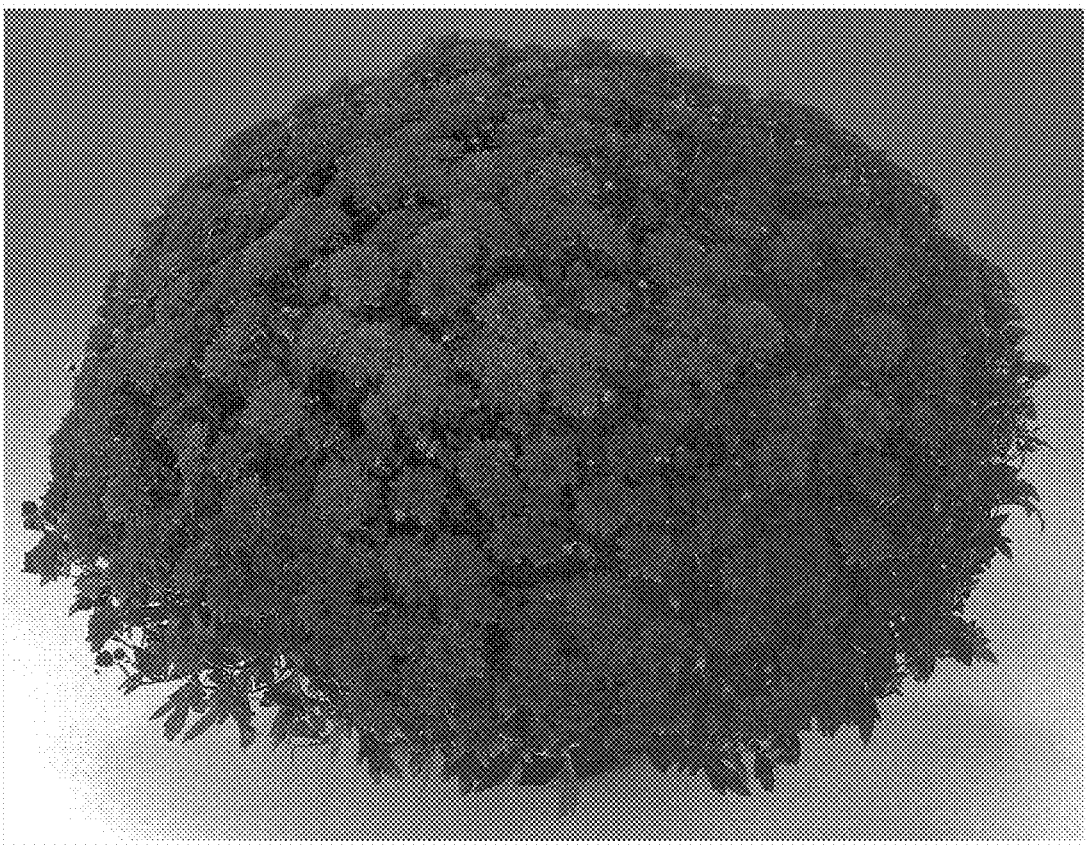

The present invention relates to a new and distinct cultivar of Chrysanthemum plant, herein after referred to by the cultivar name 'GEDI ONE CAR.'

This new cultivar was the result of hybridization of a female parent, 'Marenco' (unpatented in the United States) with an unnamed, undistributed and unpatented male parent of another cultivar. The new cultivar was selected by the inventor in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE CAR' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE CAR.' These characteristics in combination distinguish 'GEDI ONE CAR' as a new and distinct Chrysanthemum:

1. Large decorative type inflorescence;
2. Consistent flowering response to short days, blooming consistently after 49 days of short day length;
3. Free branching habit; and
4. Dark purple ray florets, which resist fading with age.

Plants of the new Chrysanthemum are similar to plants of the parent cultivars in most horticultural characteristics, however plants of the new cultivar differ from plants of the female parent cultivar 'Marenco' in the following characteristics:

1. The new cultivar has a more round plant shape;
2. The new cultivar has many more ray florets than the parent;
3. The new cultivar has individual blooms resisting fading better; and
4. The new cultivar has darker purple ray florets.

The new cultivar also differed from the male parent in the following characteristics:

1. The new cultivar has a wider diameter flower;
2. The new cultivar has many more ray florets than the parent; and
3. The new cultivar has different color ray florets.

The new cultivar can be compared to the Chrysanthemum cultivar 'CLEAGAR VZP1' (disclosed in U.S. Plant Pat. No. 11,300). However plants of the new Chrysanthemum differed from the plants of the cultivar 'CLEAGAR VZPl' in the following characteristics:

1. The new cultivar naturally blooms 2 weeks later;
2. The new cultivar has darker purple ray florets;
3. The new cultivar has a more round plant shape; and
4. The new cultivar has many more ray florets.

BRIEF DESCRIPTION OF THE PHOTOGRAPHS

The photograph shows a plant of 'GEDI ONE CAR' grown in a 2-gallon container. A single cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 135 days from rooted cuttings. The growing conditions range from 60° to 65° F. at night to 70° to 85° F. during the day. Measurements and numerical values represent averages of typical flowering types.

Botanical classification: *Dendranthema morifolium* cultivar 'GEDI ONE CAR'
Commercial classification: Garden-type Chrysanthemum
Parentage: Hybridization of female parent 'Marceno' (unpatented in the United States) and Chrysanthemum cultivar male parent (unpatented in the United States)

PROPAGATION

Type: Asexual vegetative
Time to Rooting: 7 to 14 days at approximately 21° C.
Root description: Fine, fibrous

PLANT

Growth habit: Mounding herbaceous perennial
Height: Approximately 22 cm
Growth rate: Moderate
Plant spread: Approximately 26 cm
Branching characteristics: Free Branching
Length of lateral branches: Approximately 18 cm
Number of leaves per lateral branch: Approximately 25
Stem color: Near 137A

FOLIAGE

Leaf:
*Arrangement.*—Alternate, single.
*Average length.*—Approximately 6.4 cm.
*Average width.*—Approximately 3.2 cm
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—young foliage upper side: Near 137A young foliage under side: Near 137B mature foliage upper side: Near 137A mature foliage under side: Near 137B venation upper side: Near 138C venation under side: Near 137C.

Petiole:
*Average length.*—Approximately 2.1 cm.
*Color.*—137A.
*Diameter.*—3 mm

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in September, first week in October.
*Number of inflorescences per stem.*—Approximately 12.
*Inflorescence diameter.*—Approximately 6.0 cm.
*Inflorescence depth.*—2.0 cm.
*Inflorescence longevity on plant.*—Approximately 22–26 days.
*Persistence.*—Persistent.

Ray florets:
*Appearance.*—Matte.
*Texture.*—Smooth.
*Average number per flower.*—Approximately 270.
*Shape.*—Oblanceolate.
*Margin.*—Entire.
*Apex.*—Obtuse.
*Length.*—Approximately 4 cm.
*Width.*—Approximately 1 cm.
*Color.*—upper surface at first opening: Near 71A upper surface at maturity: Near 77A upper surface at fading: Near 70A under surface at first opening: Near 71A under surface at maturity: Near 77A under surface at fading: Near 71B.

Disc florets:
*Appearance.*—Shiny.
*Texture.*—Smooth.
*Average number per flower.*—Approximately 50.
*Shape.*—Cylindric.
*Apex.*—Obtuse.
*Average length.*—Approximately 1 cm.
*Average width.*—Approximately 0.2 cm.
*Color.*—at first opening: Near 2A at maturity: Near 7A at fading: Near 17D.

Peduncle:
*Length.*—at terminal end (shortest): Approximately 6 cm at lateral end (longest): Approximately 9 cm.
*Strength.*—Moderate.
*Color.*—Near 137C.
*Habit.*—Erect.
*Surface.*—Pubescent.

Inflorescence bud:
*Length.*—Approximately 1 cm.
*Diameter.*—Approximately 1 cm.
*Form.*—Globular.
*Color.*—Near 71A.

Phyllaries:
*Appearance.*—Matte.
*Texture.*—Lightly pubescent.
*Number.*—Approximately 40 to 50.
*Shape.*—Ovate.
*Margin.*—Entire.
*Apex.*—Acute.
*Diameter.*—0.3 cm.
*Length.*—0.5 cm.
*Color.*—upper side: Near 137A under side: Near 137A.

REPRODUCTIVE ORGANS

Ray florets:
*Number of pistils per flower.*—1.
*Stigma shape.*—2 branched.
*Stigma color.*—Near 16D.
*Style color.*—Near 16D.
*Style length.*—Approximately 0.8 cm.
*Stamens.*—Absent.

Disc florets:
*Number of pistils per flower.*—1.
*Stigma shape.*—Cylindric.
*Style length.*—Approximately 0.5 cm.
*Number of stamens per flower.*—Approximately 5.
*Anther shape.*—Tubular.
*Anther color.*—Near 16A.
*Pollen color.*—Near 17B.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'GEDI ONE CAR' as herein illustrated and described.

* * * * *